United States Patent
Hoath et al.

(10) Patent No.: US 6,562,358 B2
(45) Date of Patent: *May 13, 2003

(54) NONTOXIC VERNIX COMPOSITIONS AND METHOD OF PRODUCING

(75) Inventors: Steven B. Hoath, Cincinnati, OH (US); Martha O. Visscher, Cincinnati, OH (US)

(73) Assignee: Children's Hospital Medical Center, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/850,844

(22) Filed: May 8, 2001

(65) Prior Publication Data

US 2002/0039590 A1 Apr. 4, 2002

Related U.S. Application Data

(63) Continuation-in-part of application No. 09/447,108, filed on Nov. 22, 1999, which is a continuation-in-part of application No. 09/257,008, filed on Feb. 25, 1999, now Pat. No. 6,113,932, which is a continuation-in-part of application No. 09/033,209, filed on Mar. 2, 1998, now Pat. No. 5,989,577.
(60) Provisional application No. 60/202,567, filed on May 10, 2000.

(51) Int. Cl.[7] .................................. A01N 25/35
(52) U.S. Cl. .................... 424/402; 424/401; 424/59; 424/444; 424/445
(58) Field of Search .................... 424/59, 401, 402, 424/443, 444, 445

(56) References Cited

U.S. PATENT DOCUMENTS

| | | | |
|---|---|---|---|
| 5,631,012 A | 5/1997 | Shanni | 424/401 |
| 5,874,091 A | 2/1999 | Grollier | 424/401 |
| 5,989,577 A * | 11/1999 | Hoath et al. | 424/402 |
| 6,113,932 A * | 9/2000 | Hoath et al. | 424/402 |

FOREIGN PATENT DOCUMENTS

| | | | |
|---|---|---|---|
| EP | 0 440 058 | 8/1991 | A61K/7/00 |
| EP | WO 98/01107 | 1/1998 | A61K/7/42 |
| EP | WO 99/44582 | 9/1999 | A61K/9/00 |

OTHER PUBLICATIONS

Baker et al., *Is vernix caseosa a protective material to the newborn? A biochemical approach.*, The Indian Journal of Pediatrics, vol. 62, No. 2, 1995, 237–239.

Allen and Taplin, *Tropical Immersion Foot*, The Lancet, Nov. 24, 1973, 1185–1189.

Bautista et al., *Characterization of Vernix Caseosa as a Natural Biofilm: Comparison to Standard Oil–Based Ointments*, Pediatric Dermatology, 2000, vol. 17, No. 4, 253–260.

Bettinger et al., *Opposing Effects of Glycerol on the Protective Function of the Horny Layer against Irritants and on the Penetration of Hexyl Nicotinate*, Dermatology, vol. 197, 1998, 18–24.

(List continued on next page.)

*Primary Examiner*—Jose' G. Dees
*Assistant Examiner*—Konata M. George
(74) *Attorney, Agent, or Firm*—Wood, Herron & Evans, L.L.P.

(57) ABSTRACT

A protectant composition comprising vernix for a skin curative and skin protectant effect and a method of using the composition. A natural or synthetic vernix is dispersed in an effect amount and is applied to a surface. The method may be used to repel a naturally occurring agent such as water, or a synthetic agent to which exposure may occur, for example, in an occupational setting.

25 Claims, 9 Drawing Sheets

OTHER PUBLICATIONS

Denda et al., *Low Humidity Stimulates Epidermal DNA Synthesis and Amplifies the Hyperproliferative Response to Barrier Disruption: Implication for Seasonal Exacerbations of Inflammatory Dermatoses*, The Journal of Investigative Dermatology, Nov. 1998, vol. 111, No. 5, 873–878.

El Khyat et al., *Skin Critical Surface Tension*, Skin Research and Technology, 1996, vol. 2, 91–96.

El–Shimi and Goddard, *Wettability of Some Low Energy Surfaces*, Journal of Colloid and Interface Science, vol. 48, No. 2, Aug. 1974, 242–247.

Emery et al., *The Relationship Between Skin Maturation and Electrical Skin Impedance*, Journal of Dermatological Science, 1991, vol. 2, 336–340.

Ghadially et al., *Effects of Petrolatum on Stratum Corneum Structure and Function*, Journal of the American Academy of Dermatology, Mar. 1992, vol. 26, No. 3, 387–396.

Ginn et al., *The Contact Angle of Water on Viable Human Skin*, Journal of Colloid and Interface Science, 1968, vol. 26, 146–151.

Haahti et al., *Fatty Acids of Vernix Caseosa*, Scandinavian Journal of Clinical and Laboratory Investigation, 1961, vol. 13, 70–73.

Hardman et al., *Barrier Formation in the Human Fetus is Patterned*, The Journal of Investigative Dermatology, Dec. 1999, vol. 113, No. 6, 1106–1113.

Hiemenz and Rajagopalan, *Surface Tension and Contact Angle: Application to Pure Substances*, In: Principles of Colloid and Surface Chemistry, New York: Marcel Dekker, 3rd ed., 1997, 248–296.

Janczuk et al., *On the Consistency of Surface Free Energy Components as Calculated from Contact Angles of Different Liquids: An Application to the Cholesterol Surface*, Journal of Colloid and Interface Science, 1993, vol. 159, 421–428.

Karkkainen et al., *Lipids of Vernix Caseosa*, The Journal of Investigative Dermatology, 1965, vol. 44, No. 5, 333–338.

Kligman, *Hydration Injury to Human Skin*, In: Van der Valk, PGM and Mailbach, HI, eds. The Irritant Contact Dermatitis Syndrome, Boca Raton, Florida: CRC Press, 1996, 187–194.

Martin, *Interfacial Phenomena*, In: Martin, A., eds., Physical Pharmacy, 1993: Chapter 4, 362–392.

Mavon et al., *Sebum and Stratum Corneum Lipids Increase Human Skin Surface Free Energy as Determined from Contact Angle Measurements: A Study on Two Anatomical Sites*, Colloids and Surfaces B: Biointerfaces, 1997, vol. 8, 147–155.

Mize et al., *The Relationship Between Postnatal Skin Maturation and Electrical Skin Impedance, Arch Dermatol*, May 1989, vol. 125, 647–650.

Myers, *Wetting and Spreading*, In: Myers, D., ed. Surfaces, Interfaces, and Colloids: Principles and Applications, New York: Wiley, V.C.H. 1999, 2nd Ed., Chapter 17, 415–447.

Narendran et al., *Interaction Between Pulmonary Surfactant and Vernix: A Potential Mechanism for induction of Amniotic Fluid Turbidity*, Pediatric Research, 2000, vol. 48, No. 1, 120–124.

Nicolaides et al., *The Fatty Acids of Wax Esters and Sterol Esters from Vernix Caseosa and from Human Skin Surface Lipid*, Lipids, 1972, vol. 7, No. 8, 506–517.

Nopper et al., *Topical Ointment Ttherapy Benefits Premature Infants*, The Journal of Pediatrics, 1996, vol. 128, No. 5, Part 1, 660–669.

Owens and Wendt, *Estimation of the Surface Free Energy of Polymers*, Journal of Applied Polymer Science, 1969, vol. 13, 1741–1747.

Pickens et al., *Characterization of Vernix Caseosa: Water Content, Morphology, and Elemental Analysis*, The Journal of Investigative Dermatology, Nov. 2000, vol. 115, No. 5, 1–7.

Rosenberg et al., *Interaction Forces Involved in Wetting of Human Skin*, Journal of Pharmaceutical Sciences, Jun. 1973, vol. 62, No. 6, 920–922.

Saijo and Tagami, *Dry Skin of Newborn Infants: Functional Analysis of the Stratum Corneum*, Pediatric Dermatology, Jun. 1991, vol. 8, No. 2, 155–159.

Schaefer and Redelmeier, *Composition and Structure of the Stratum Corneum in Skin Barrier: Principles of Percutaneous Absorption*, (Kargur, New York) 1996, 43–86.

Sumida et al., *Studies on the Function of Vernix Caseosa: The Ssecrecy of Baby's Skin*, Preprints of the IFSCC 20th International Conference, Cannes, France, 1998.

Tsai and Maibach, *How Irritant is Water? An Overview*, Contact Dermatitis, 1999, vol. 41, 311–314.

Visscher et al., *Early Adaptation of Human Skin Following birth: A Biophysical Assessment*, Skin Research and Technology, 1999, vol. 5, 213–220.

Wigger–Alberti and Elsner, *Petrolatum Prevents Irritation in a Human Cumulative Exposure Model in Vivo*, Dermatology, 1997, vol. 194, 247–250.

Wilson and Maibach, *A Review of Transepidermal Water Loss*, In: Maibach and Boisits, Eds. Neonatal Skin: Structure and Function. New York: Marcel Dekker. 1982: 83–100.

T. Yamamoto and Y. Yamamoto. *Electrical Properties of the Epidermal Stratum Corneum*, Medical and Biological Engineering, Mar. 1976, 151–158.

Youssef et al., *Surface Free Energy Characterization of Vernix Caseosa. Potential Role in Waterproofing the Newborn Infant*, Skin Research and Technology, 2001, vol. 7, 10–17.

\* cited by examiner

NONTOXIC VERNIX COMPOSITIONS AND METHOD OF PRODUCING

RELATED APPLICATION

This application claims priority from U.S. Provisional Application Ser. No. 60/202,567 filed May 10, 2000, which is a Continuation-In-Part of U.S. patent application Ser. No. 09/447,108 filed Nov. 22, 1999, which is a Continuation-In-Part of U.S. patent application Ser. No. 09/257,008 filed Feb. 25, 1999, now U.S. Pat. No. 6,113,932, which is a Continuation-In-Part of U.S. patent application Ser. No. 09/033,209 filed Mar. 2, 1998, now U.S. Pat. No. 5,989,577.

FIELD OF THE INVENTION

The invention relates generally to a therapeutic or prophylactic vernix composition and method.

BACKGROUND OF THE INVENTION

Skin is one of the largest organs in the body and covers substantially the entire body surface. Skin is composed of two main layers: the surface epithelium or epidermis which includes the uppermost stratum corneum, and the subjacent connective tissue layer or dermis. The skin has a number of functions such as protecting an organism from injury and dessication, receiving environmental stimuli, excreting various substances, regulating body temperature and helping to maintain water balance. Because of its quantitative and qualitative importance, substantially intact and healthy skin is crucial not only for the well being of an organism but for its very survival.

The health and integrity of skin may be compromised by wounds, abrasions, ulcers, burns, infections, irritations, premature birth and other conditions for which normal skin production and repair processes may be inadequate. For example, acute conditions such as patients who are burned over a large surface area often require immediate skin replacement. Less life-threatening but chronic skin problems such as decubitus ulcers or irritations from diaper rash may progress to more severe conditions if left untreated or if they occur in a neonate or a geriatric patient. Skin treatments encompass a variety of methods and products. These may range from symptomatic treatments such as the use of topical anti-inflammatory compounds to the use of replacement skin. For various physiological, medical, and other reasons, however, none of these treatments meet the desired goal of utilizing the body's own healing and repair system to promote and regulate its own skin growth and maturation.

Exposure of the skin to water over a prolonged time period produces deleterious effects on the integrity and condition of the skin, such as maceration and damage to the barrier function of skin. For example, long term water exposure is a known cause of dermatitis. Dermatitis, defined as an inflammation of the skin, is a major problem in professions in which a portion of the skin is subject to prolonged water exposure (the so-called "wet professions"). Soldiers serving in tropical climates are also known to suffer from painful swollen feet ("tropical immersion foot") due to long term water exposure. Such situations comprise a large part of occupational medicine and have a significant economic impact. Thus, there is a need for treatment and prevention of these deleterious effects on the skin.

Vernix caseosa (vernix) is a naturally occurring skin protectant. Vernix is a lipid rich substance composed of sebum, epidermal lipids, and desquamated epithelial cells that progressively covers the skin of the developing fetus, completely surrounded by amniotic fluid, during the last trimester of pregnancy.

Vernix consists of hydrated cells dispersed in a lipid matrix. This lipid matrix undergoes a transition to a more fluid form at physiological temperatures and with the application of shear forces, such as those encountered with movement. Vernix is a covering for the skin of the fetus that resembles the stratum corneum except that it lacks multiple rigid desmosomal connections. Consequently, vernix exhibits a viscous fluid character, making controlled management and/or application to a surface difficult.

A need thus exists for a formulation that can be applied to a biological surface such as skin for treatment and prevention of conditions related to skin surface properties.

SUMMARY OF THE INVENTION

The invention is directed to a method to enhance hydrophobicity of a biological surface by applying a composition of vernix and a dispersing agent to the surface. The composition is applied to the surface, e.g., skin, in an amount effective to enhance hydrophobicity. Vernix, natural and/or synthetic, may be formulated as a cream, a lotion, a gel, an ointment, etc.

The invention is also directed to a method to regulate skin hydration by applying a composition of vernix and a dispersing agent to the skin in an amount effective to regulate hydration. The method may be used on developing skin, such as wounded skin or skin on a preterm newborn.

The invention is also directed to a method to enhance skin repair by regulating the water gradient of skin with a composition of vernix and a dispersing agent in an amount effective to regulate the water gradient. The composition may be used to repair trauma from a physical or chemical source.

The invention is also directed to a method to enhance hydrophobicity of a biological surface by applying a vernix film to the surface in an amount effective to achieve a surface free energy of at least about 20 dyne/cm. In one embodiment, the vernix is applied in an amount to achieve a surface free energy of about 40 dyne/cm.

These and other methods and compositions will be apparent in light of the following drawings, detailed description and examples.

DETAILED DESCRIPTION

Figure 1:
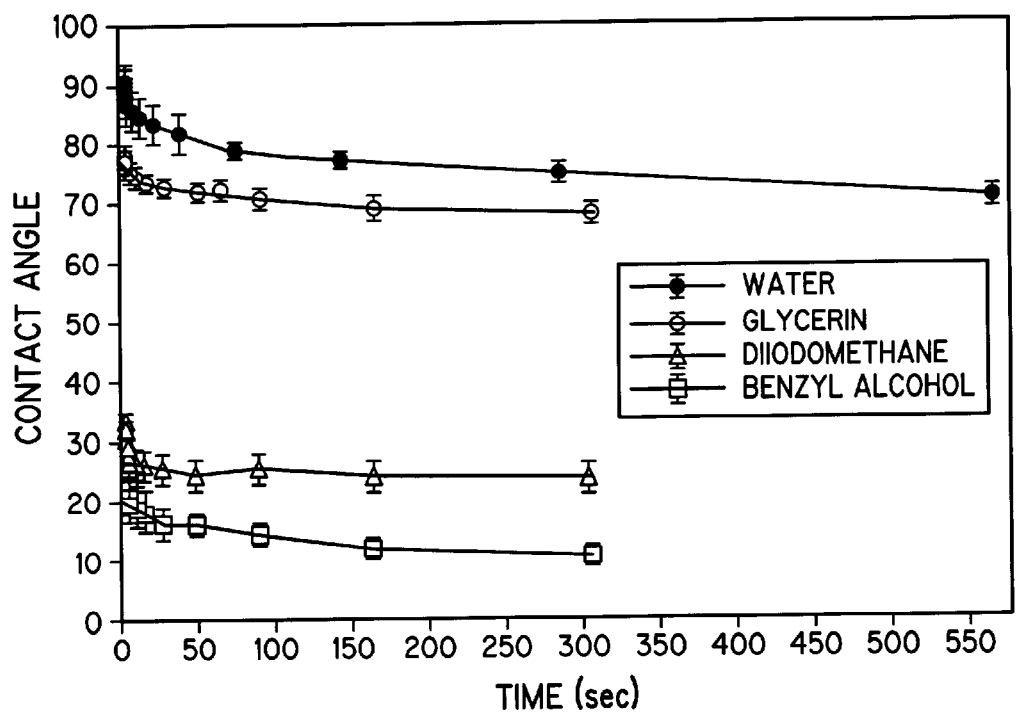
FIG. 1 is a graph of change of contact angle with time for various liquids applied to a vernix film.

A protectant composition of tractable vernix is disclosed. One protectant effect is by the action of vernix as a repellant to one or more agents. The agent may be a natural compound, e.g., water, or a partially or totally synthetic compound, e.g., a fungicide, rodenticide, and/or insecticide. The term "repellant" includes any enhanced degree of repellence over that obtained in the absence of the inventive composition. While the extent of repellence may be either partial or complete, any enhancement over the untreated state is considered an improvement and is included in the invention.

Application of the composition to the desired surface may be prophylactic, so that the composition is applied to the skin or other surface before exposure to the agent occurs. Application of the composition may be curative, for example, to further protect a compromised skin surface or to provide a protectant surface during natural or mediated healing of an exposed skin surface. Application of the composition may be protective, for example, to protect a skin surface should exposure to the agent occur.

Protectant vernix compositions may contain natural or synthetic vernix. A synthetic vernix composition may be partially or totally synthetic. Natural vernix was obtained from a newborn infant at the time of delivery. Vernix comprises about a 10% lipid fraction by weight, about a 10% protein fraction by weight, and about an 80% volatile fraction by weight. The lipid fraction has been reported to comprise lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). The lipid fraction may contain, with the relative percentages indicated, squalene (9%), aliphatic waxes (12%), sterol esters (33%), diesters (7%), triglycerides (26%), free sterols (9%), and other lipids (4%). The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor, and trace amounts of about nanomolar to micromolar concentrations of surfactant protein such as Surfactant A and Surfactant B. The volatile fraction is primarily water. The rate of evaporation of volatile components is relatively slow, presumably due to increased energy requirements for the dissociation of hydrogen bonds and for diffusion from the cellular component through the lipid component to change water from the liquid to the gaseous state. Vernix is an odorless material, indicating the absence of volatile carbon or nitrogen containing compounds.

Synthetic vernix may be produced by mixing one part of natural vernix, removed from an infant at the time of delivery, with any of the following components in the proportions indicated: either about 0.005 to about 0.05 parts phospholipid, or trace amounts of about nanomolar to micromolar concentrations of pulmonary surfactant proteins such as Surfactant A and/or Surfactant B, or 5 parts dimethylsulfoxide (DMSO), or 1 part amniotic fluid, or combinations of the above. Alternatively, synthetic vernix may also be produced by combining lipids to comprise about a 10% fraction of the entire volume, proteins to comprise about a 10% fraction of the entire volume, and water to comprise the remaining about 80% of the entire volume. The following lipid components are combined in the relative percentages indicated: squalene (9%), aliphatic waxes (12%), sterol esters (33%), diesters (7%), triglycerides (26%), free sterols (9%), and other lipids (4%). The fatty acids within the waxes may be branched and the branched fatty acids may be methylated. The protein components, combined to constitute about a 10% fraction, are epidermally derived proteins, primarily keratin and filaggrin, with trace amounts of about micromolar to millimolar concentrations of regulatory proteins such as epidermal growth factor, and trace amounts of about nanomolar to micromolar concentrations of surfactant protein such as Surfactant A and Surfactant B.

In one embodiment, vernix dispersed in a biocompatible liquid was applied to a physiologically acceptable support structure in a liquid state to form a repellent vernix film. A film is defined herein as a surface and/or interfacial covering, in either a liquid or a solid state, with temperature-dependant properties. Film-forming techniques include but are not limited to spraying, extruding, blowing, pouring, evaporating, coating and painting. The vernix dispersion is presented as droplets which coalesce to form a film upon encountering the support.

In an alternate embodiment, a preformed vernix repellent film is applied to a support. The physiologically acceptable support structure is one that can withstand sterilization, preferably by standard sterilization techniques known to one skilled in the art such as exposure to gamma radiation, autoclaving, and so on. The support structure is not limited to a particular composition or configuration and, depending upon its use, may or may not be sterilized and may take various forms.

In another embodiment, the nontoxic vernix film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II® (Sterling Drug Inc., New York, N.Y.) or circular nylon filters of suitable porosity (Micron Separations Inc., Westboro, Mass.). Other support materials, however, could also be used to practice the invention.

In another embodiment, the nontoxic vernix repellent film is used to treat or prevent injury due to substance exposure or trauma, and may be applied to various materials for placement either in direct contact or indirect contact with an exposed skin site. The skin site may be intact (e.g., normal skin) or may be compromised, defined as skin that is damaged or that lacks at least some of the stratum corneum (e.g., skin damaged by exposure to the agent in question, another agent, the presence of a pathological condition such as a rash or contact dermatitis, a physical trauma such as a cut, wound, or abrasion, a underdeveloped skin such as occurs in a preterm infant, conditions in which either all or part of the epidermis is exposed, conditions in which part of the dermis has been removed such as partial thickness wounds encountered in resurfacing procedures such as chemical peels, dermabrasions, and laser resurfacing, etc.).

The support structure may be permeable to physical and/or chemical agents, and may take a variety of forms, depending upon its purpose and the extent of the area requiring dressing or treatment. The nontoxic vernix film may be applied to various synthetics such as thermoplastic films, blown films and breathable films, and various natural and synthetic fabric compositions such as woven, nonwoven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

At least one role of vernix is to "waterproof" the fetus during this critical period of epidermal barrier development, cornification of the epidermis to form the stratum corneum, before birth. Infants born prematurely have little or no stratum corneum barrier, and are essentially born with compromised skin.

The interaction of exogenous agents, such as water or other agents, with vernix is related to the nonpolar (dispersive) and polar (nondispersive) components of vernix and the critical surface tension (CST) of vernix. Water has a relatively high CST (72 dynes/cm). The hydrophobicity (i.e., relatively low CST) of vernix was unanticipated, since about 80% by weight of natural vernix is water. The nonpolar component (lipids) of vernix is substantially higher than the polar component (cells, which contribute proteins), and confers hydrophobicity to vernix since the lipid component is a continuous phase surrounding the cellular components with which water is associated. In comparison to a known hydrophobic material and skin protectant, petrolatum, which has an extremely high nonpolar component, the nonpolar component of vernix is only slightly lower. In addition, the CST of both vernix and petrolatum are comparable. As a result, application of vernix to a surface such as skin, either normal skin or compromised skin (for example, wounded, abraded, cut, punctured, etc.), would protect the surface from the effects of water exposure. The waterproofing effects could be particularly useful during repeated cycles of skin exposure to water followed by drying, such as occurs with health care professionals performing repeated hand washings.

A result of the low CST of vernix is that little interaction between vernix and hydrophilic liquids would be expected to occur. For example, there would be expected to be little interaction between a vernix-treated surface, such as skin or a substrate to which vernix has been provided, that is exposed to an exogenous hydrophilic liquid, such as water, saline, urine, etc. The low CST of vernix imparts a hydrophobic character to vernix with respect to these liquids, and hence vernix serves as a protectant against the effects of these liquids.

A surface to which vernix has been applied, either directly or indirectly, and then exposed to nonpolar agents such as oils, would be expected to be at least somewhat miscible with the lipid component of vernix. As described in U.S. Pat. No. 5,989,577 and co-pending application Ser. No. 09/257,008, now U.S. Pat. No. 6,113,932, and Ser. No. 09/447,108, each of which are expressly incorporated by reference herein in their entirety, the water in vernix is associated with cells, and the cells are embedded within the lipid material, thus, the lipid component presents vernix to the environment. However, if the lipid fraction is removed either partially or totally by exposure to hydrophobic agents, then the water rich fraction, such as cells, could be exposed to the environment. The inventive composition could be regulated to have a higher polar component and would repel nonpolar agents. This composition would be a protectant to nonpolar materials, even after the hydrophobic lipid components were modified through interaction with the environment.

In the developing fetus, vernix protects the skin by preventing water surrounding the fetus from removing essential ingredients, such as enzymes, calcium binding proteins, natural moisturizing factors, ions, etc., required for barrier development. In much the same way, a vernix treated surface such as skin is protected from exogenous water by preventing removal of essential ingredients from the surface. For example, vernix could protect extraction of natural moisturizing factors in the upper stratum corneum by water.

Another role of vernix is to protect the developing skin from the deleterious effects of substances, such as water, urine, and feces, present in utero during gestation. The inventive vernix composition may be applied to any biological surface whereby a surface energy of about 40 dynes/cm is beneficial for repelling exogenous agents. Thus, an effective amount of vernix is that which achieves a surface free energy of about 40 dynes/cm, to a minimum of about 20 dynes/cm. For example, applying the inventive vernix composition in an effective amount to the diaper area protects this skin from the damaging effects of fecal material. Feces contain protease and lipase enzymes which can damage the skin surface upon contact. Lowering the surface energy of this skin surface by applying the inventive vernix composition would provide protection against contact with the water-containing feces.

The above information will be further appreciated in light of the following Examples.

EXAMPLE 1

To determine the surface characteristics of vernix, for example, its repellant properties, its barrier function, etc., the surface free energy (SFE) of vernix was calculated and analyzed for its polar (nondispersive) and nonpolar (dispersive) components using the Owens/Wendt geometric mean method. This was done by measuring the contact angle ($\theta$) between vernix and various liquids such as benzyl alcohol, diiodomethane, glycerol, and water. The critical surface tension (CST) of vernix was calculated using Zisman plots. The CST of vernix provides general information of its interaction with liquids.

Static and dynamic contact angle measurements were performed using a contact angle goniometer and FTA 200 dynamic contact angle analyzer (First Ten Angstroms, Portsmouth, Va.), respectively. Liquids (benzyl alcohol, diiodomethane, glycerol, and water) were dispensed using 24 gauge blunt end stainless steel needles (Kahnetics Dispensing Systems, Bloomington, Calif.) for the dynamic contact angle study. For the static contact angle measurements, a Microdispenser (Drummond, Broomall, Pa.) was used. Vernix was spread into films using Accuragate applicator #12 with a 0.5 inch applicating gate (Cheminstruments, Fairfield, Ohio).

Vernix was collected from term newborns, pooled (three to four newborns) and stored at 4° C. in plastic dishes sealed with Parafilm® until use. Vernix was spread into a uniform film over a polycarbonate plate using a mechanical Teflon-coated applicator with a 0.5 inch wide precision ground gate centered on the edge (Cheminstruments, Fairfield, Ohio). This restricted passage channeled the flow of vernix through the gate while metering the thickness of the applied film. The film thickness depended upon the depth of the gate and the angle at which the applicator blade was held. The applicator was held at a 45° angle during application. The film thickness was 3 mils (76.2 $\mu$m).

One drop (5 $\mu$l) of the desired liquid was manually dispensed using a microdispenser onto the vernix film. The contact angle was measured manually 25–30 seconds after the drop was applied using a magnifying telescope. The analysis for each liquid was performed in triplicate, and contact angle values were averaged. The experiment was performed on fresh vernix (one week old) and seven week old vernix. The experiment was repeated with a film of petrolatum (Witco, Petrolia, Pa.), a widely used hydrocarbon skin protectant derived from petroleum, replacing the vernix film to contrast the results obtained with vernix. The experiments were performed under controlled temperature (24° C.±1° C.) and relative humidity (50%±5%).

For dynamic contact angle measurements, liquids were preloaded into a clean 10 ml syringe fitted with a 24 gauge blunt end stainless steel needle (internal diameter=0.292 mm). Computer software controlled the dispensing rate (0.3 $\mu$l/sec) and the drop image appeared on the screen and was captured for image analysis using software provided with the goniometer.

About ten images were taken over 300 seconds (at about 0, 0.5, 0.75, 1.3, 2.3, 4.2, 7.5, 26, 48, 89, 164, and 304 sec after the drop was delivered onto the surface) for benzyl alcohol, diiodomethane, and glycerol. For water, ten images were taken over about 560 seconds to investigate the possible decline in the contact angle of water over time.

The results of the static contact angle for fresh vernix, seven week old vernix, and petrolatum are as follows, indicated as mean ± standard deviation (SD):

Contact angle data for fresh and 7-week old vernix and petrolatum

|  | Fresh vernix | | 7-week old vernix | | Petrolatum | |
| --- | --- | --- | --- | --- | --- | --- |
|  | Angle | SD | Angle | SD | Angle | SD |
| Benzyl Alcohol | 21.8 | 2.9 | 19.6 | 1.6 | 34.4 | 3.0 |
| Diiodomethane | 36.2 | 2.1 | 31.8 | 1.8 | 38.4 | 2.2 |
| Glycerol | 74.3 | 1.9 | 74.2 | 2.3 | 79.1 | 2.1 |
| Water | 83.5 | 0.8 | — | — | — | — |

Changes of contact angle with time are shown in FIG. 1. Errors bars indicate the standard deviation of three measurements; one way ANOVA analysis was used for diiodomethane, glycerol, and water, and Kruskal-Wallis ANOVA on Ranks was used for benzyl alcohol.

For benzyl alcohol, glycerol, and water, the drop in contact angle over time was significant (p<0.01). For diiodomethane, the drop in contact angle over time was not significant (p=0.834).

The change of dynamic contact angle with time (300 sec for benzyl alcohol, diiodomethane, and glycerol; 560 sec for water) may be due to liquid evaporation. Evaporation may be a particular problem with highly volatile liquids such as benzyl alcohol, and/or extended measurement time periods such as with water. Shrinking of the drop may change the contact angle from advancing to receding; receding contact angles are generally smaller than advancing contact angles. Alternatively, some molecular components of vernix may dissolve into the drop during the contact time between the liquid and the vernix layer, causing contamination and a decrease in contact angle. With a 5 $\mu$l drop of liquid, any contamination from soluble vernix components could cause a significant decrease in the surface tension of the liquid and the contact angle. Still another alternative is that the liquid is absorbed into the vernix layer, which could explain the absence of a decrease in contact angle with time using diiodomethane, a totally nonpolar hydrophobic liquid.

Figure 2A:
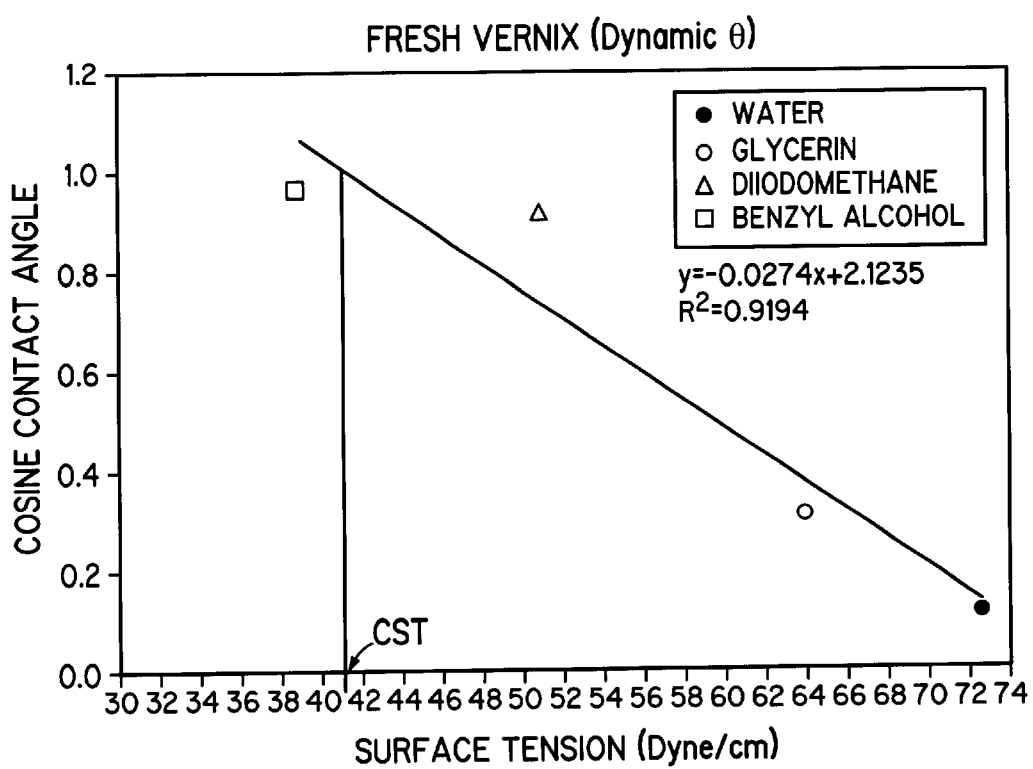
FIG. 2A is a graph of dynamic contact angle measurements for various liquids applied to a fresh vernix film.
Figure 2B:
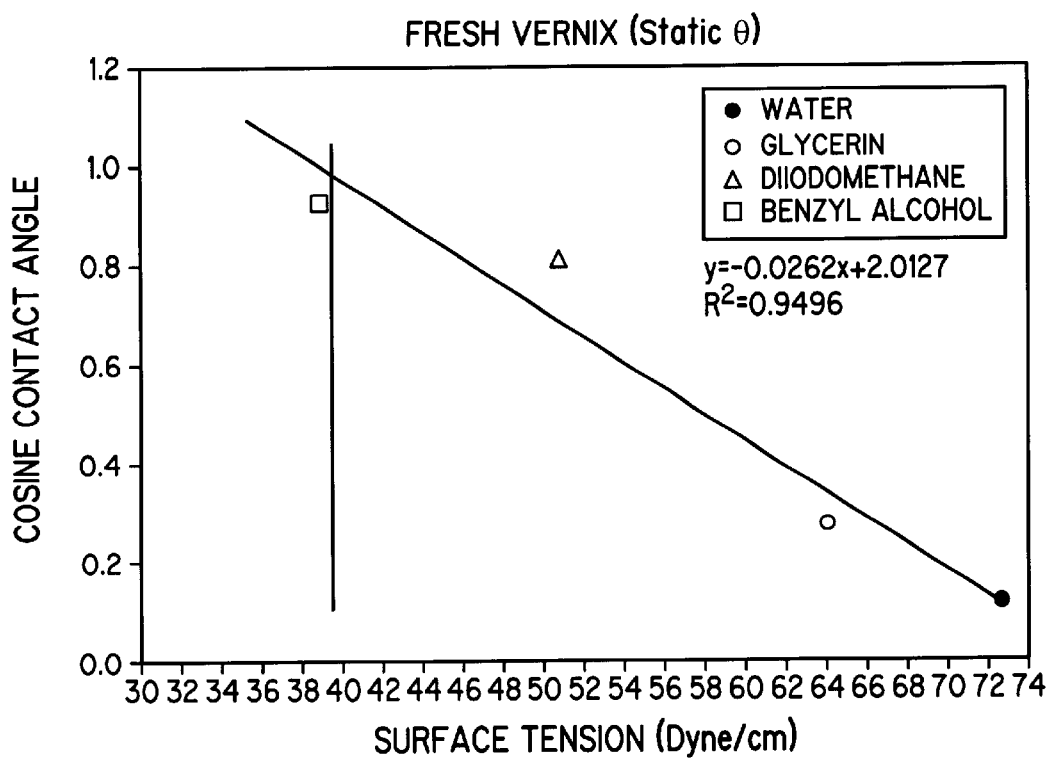
FIG. 2B is a graph of static contact angle measurements for various liquids applied to a fresh vernix film.
Figure 2C:
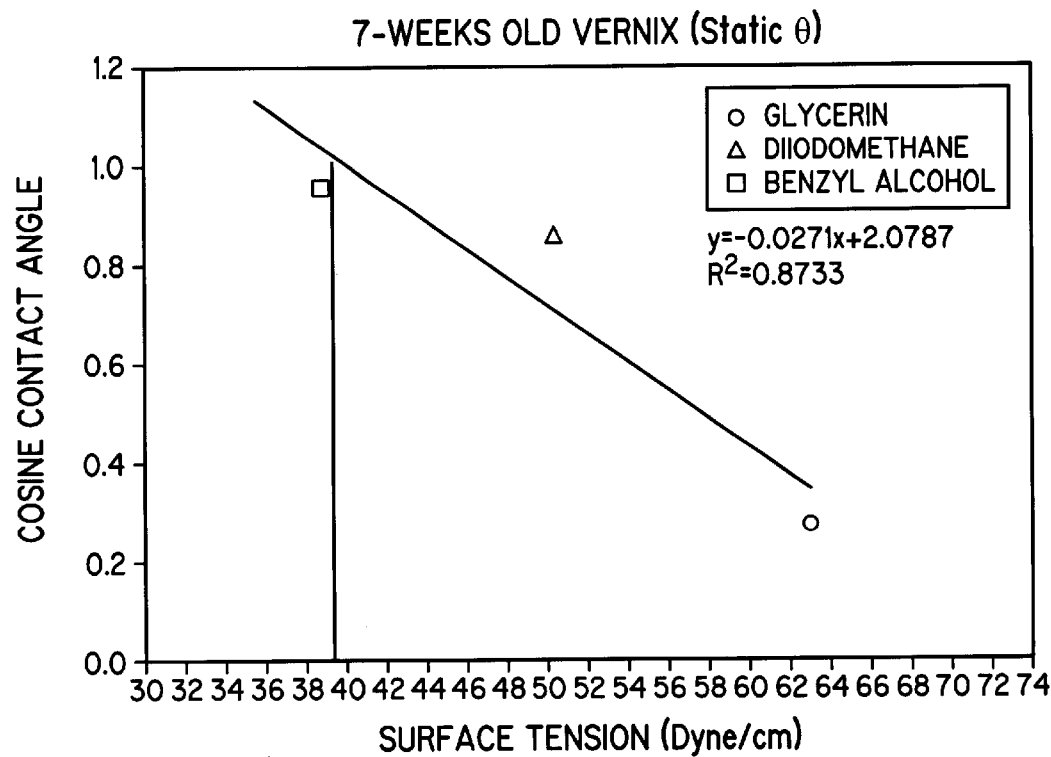
FIG. 2C is a graph of static contact angle measurements for various liquids applied to a seven week old vernix film.
Figure 2D:
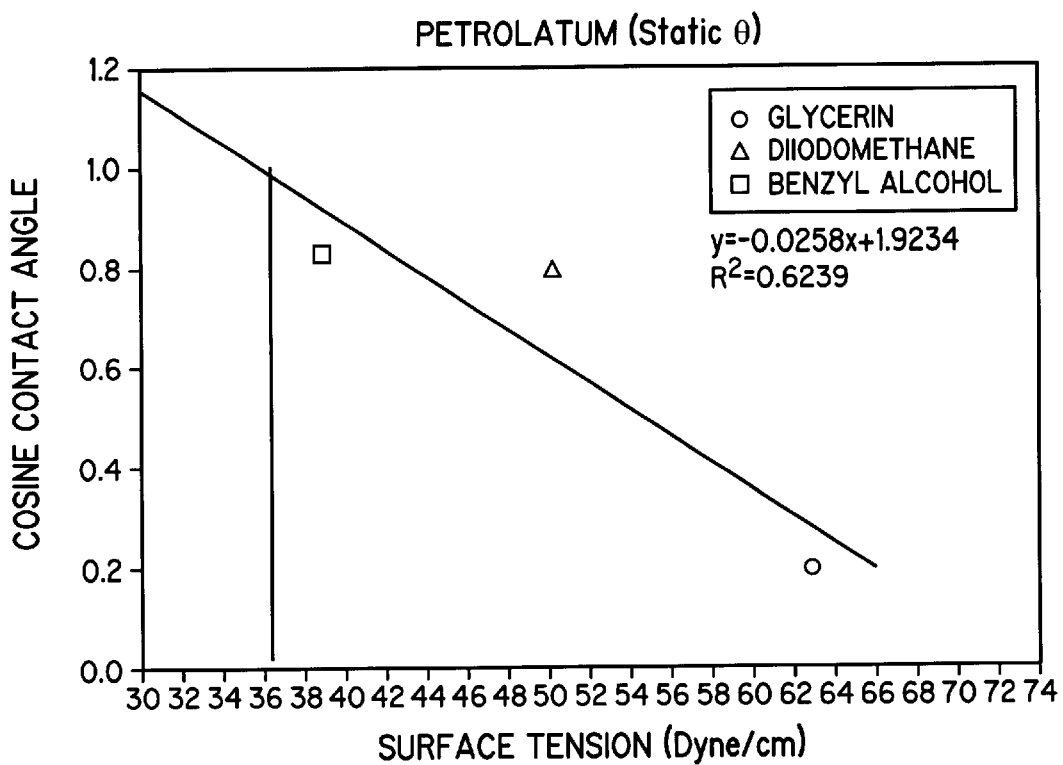
FIG. 2D is a graph of static contact angle measurements for various liquids applied to a petrolatum film.

The Critical Surface Tension (CST) was obtained by plotting surface tension of diiodomethane, glycerol, water, and benzyl alcohol versus the cosine of the dynamic contact angle on a fresh vernix film (FIG. 2A), static contact angle on a fresh vernix film (FIG. 2B), static contact angle on seven week old vernix (FIG. 2C), and static contact angle on petrolatum (FIG. 2D). Contact angles were measured at 25 sec after dispensing the liquid. Results from measurement of the dynamic contact angle of water on fresh vernix were fitted into a cubic polynomial equation and the contact angle was calculated. In all plots, a linear regression line was fitted and the value of surface tension at $\cos \theta = 1 (\theta = 0)$ was calculated from the resulting regression equation, which corresponded to the CST. These data are as follows:

|  | CST (dyne/cm) |
| --- | --- |
| Fresh vernix (dynamic $\theta$) | 40.47 |
| Fresh vernix (static $\theta$) | 38.65 |
| 7-week old vernix (static $\theta$) | 39.80 |
| Petrolatum (static $\theta$) | 35.79 |

CST is a "wettability index" that indicates the minimum value of surface tension needed for a liquid to spread completely (that is, have a contact angle of zero), on a particular surface material. Any liquid whose surface tension is equal to or less than the CST will make a zero contact angle ($\theta = 0$, $\cos \theta = 1$), and will completely spread on the surface, while any liquid having a surface tension greater than the CST will form drops with a finite contact angle.

To determine the CST of vernix, Zisman's CST was measured. CST is then calculated by extrapolating the contact angle data of various liquids, having a known surface tension on vernix, back to where the contact angle is zero.

The following equation was used to categorize vernix into its dispersive and polar components:

$$W_a = \gamma_L(\cos \theta + 1) = 2(\gamma_L{}^D \gamma_S{}^D)^{1/2} + 2(\gamma_L{}^P \gamma_S{}^P)^{1/2}$$

Work of adhesion ($W_a$) is the energy required to break the attraction between like molecules. Rearranged into the formula for a straight line, the equation is:

$$\frac{\gamma_L(\cos\theta + 1)}{2(\gamma_L^D)^{1/2}} = (\gamma_S^P)\frac{(\gamma_L^P)^{1/2}}{(\gamma_L^D)^{1/2}} + (\gamma_S^D)^{1/2}$$

$$Y = mX + b$$

Figure 3A:
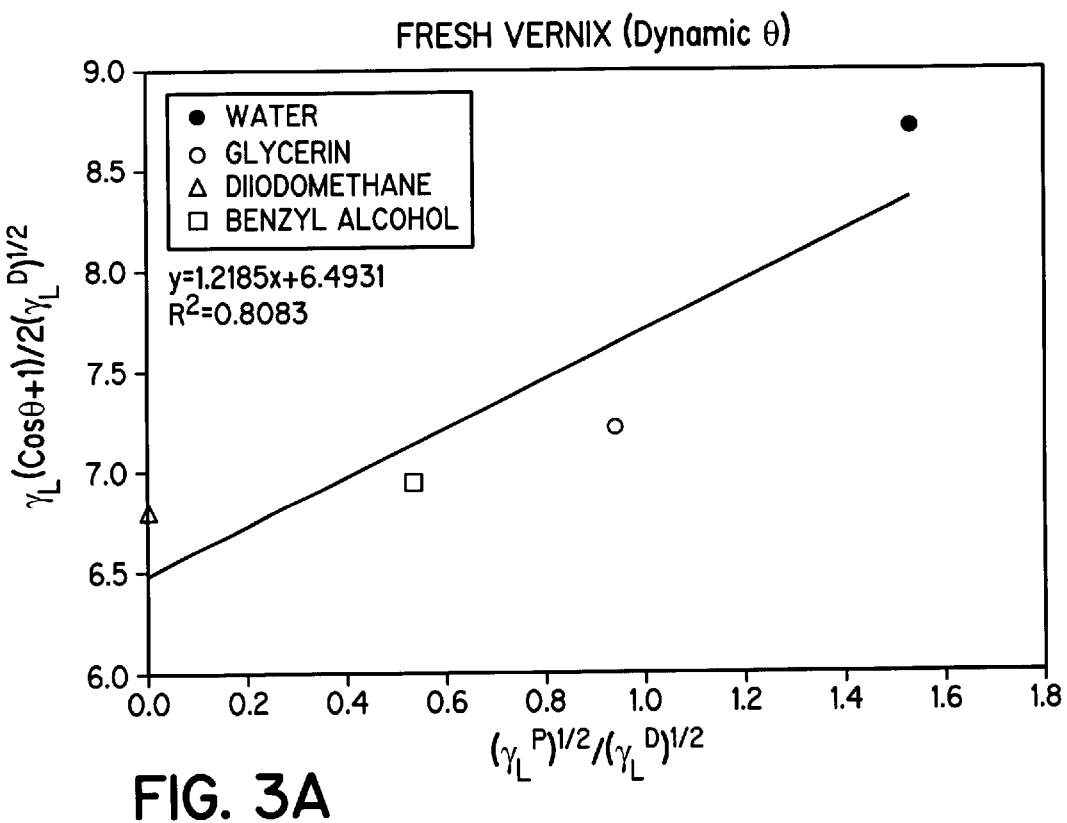
FIG. 3A is a graph of dynamic contact angle measurements for various liquids applied to a fresh vernix film.
Figure 3B:
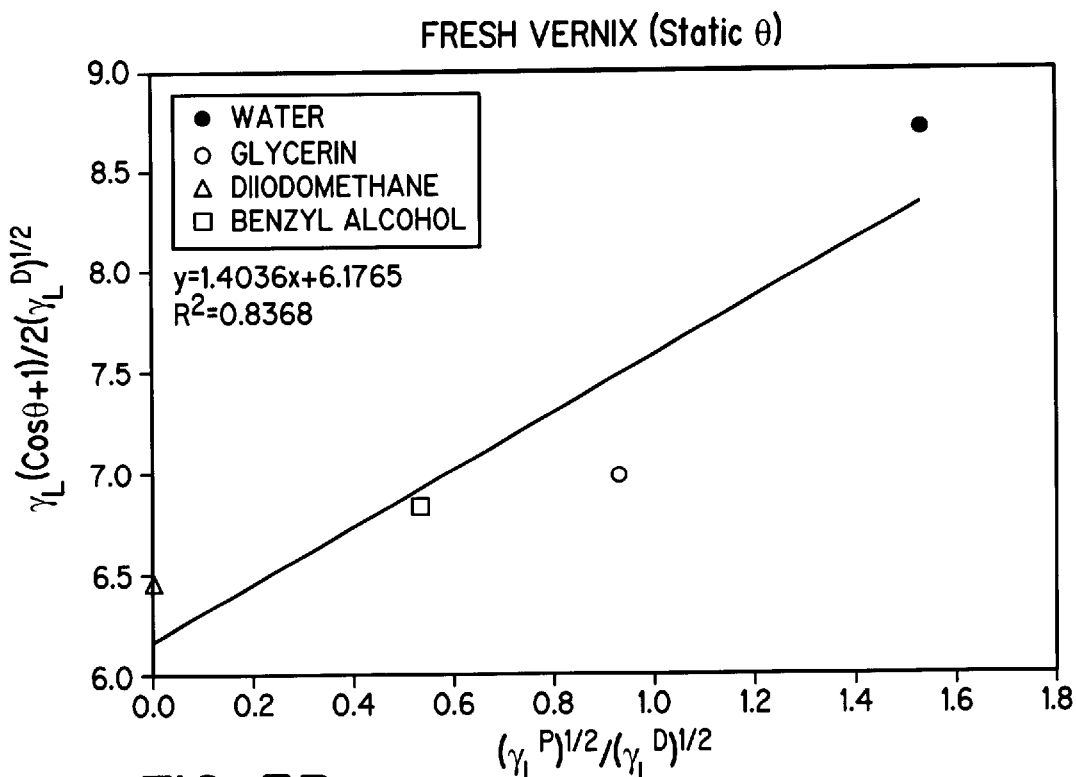
FIG. 3B is a graph of static contact angle measurements for various liquids applied to a fresh vernix film
Figure 3C:
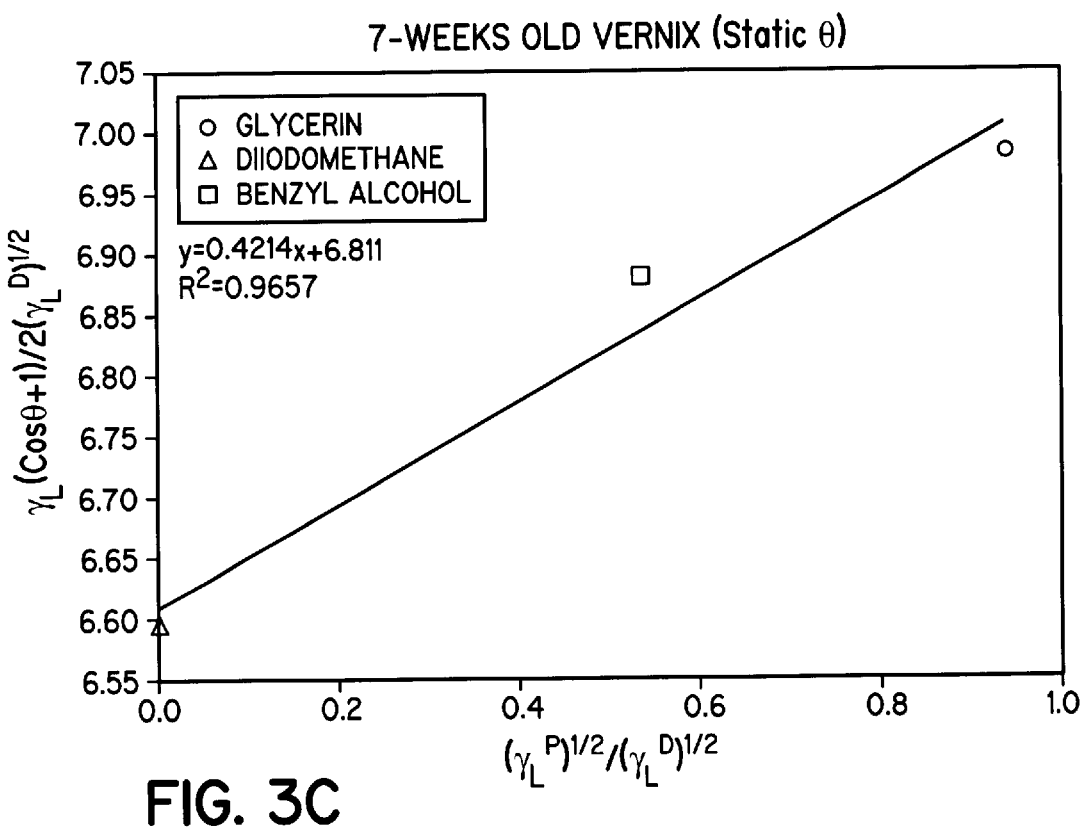
FIG. 3C is a graph of static contact angle measurements for various liquids applied to a seven week old vernix film.
Figure 3D:
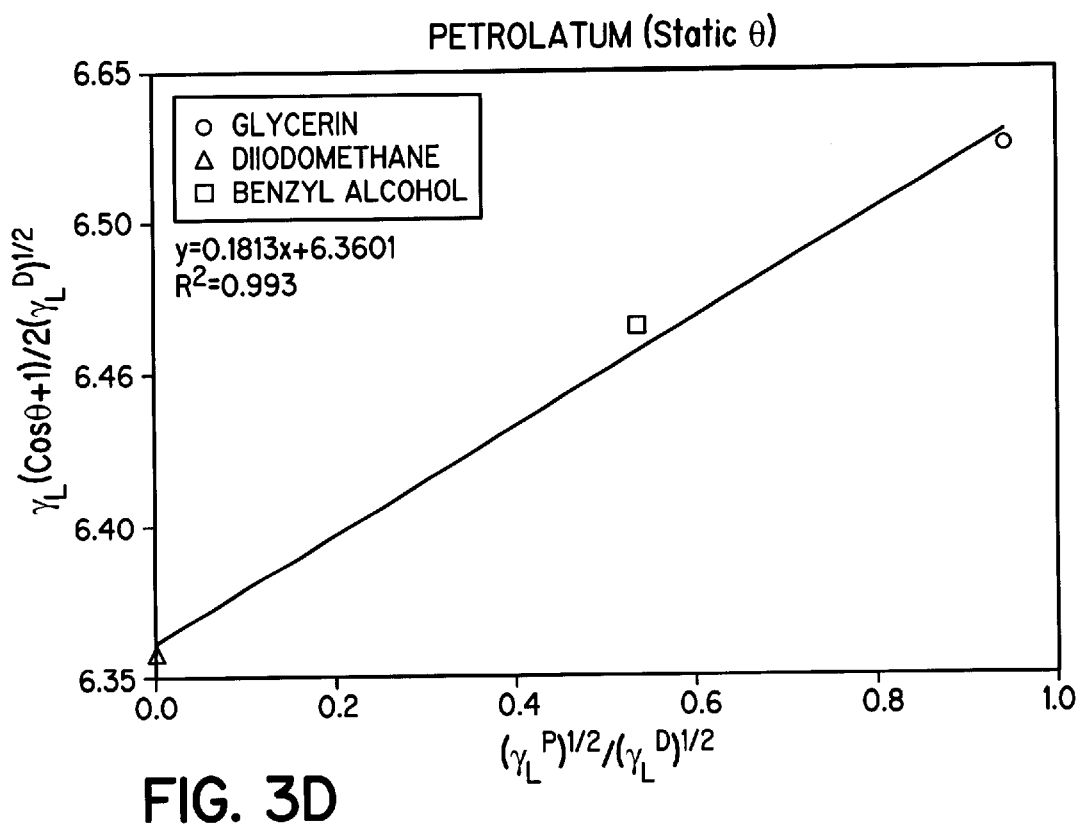
FIG. 3D is a graph of static contact angle measurements for various liquids applied to a petrolatum film.

The resulting linear regression equation was plotted for diiodomethane, glycerol, water, and benzyl alcohol of the dynamic contact angle on a fresh vernix film (FIG. 3A), static contact angle on a fresh vernix film (FIG. 3B), static contact angle on seven week old vernix (FIG. 3C), and static contact angle on petrolatum (FIG. 3D). The results are provided in the following table.

A summary of surface tension components (Owens/Wendt analysis)

| | $\gamma_L^D$ (dyne/cm) | $\gamma_L^P$ (dyne/cm) | Total (dyne/cm) |
|---|---|---|---|
| Fresh vernix (dynamic θ) | 42.16 | 1.48 | 43.64 |
| Fresh vernix (static θ) | 38.14 | 1.97 | 40.11 |
| 7-week old vernix (static θ) | 43.71 | 0.18 | 43.89 |
| Petrolatum (static θ) | 40.44 | 0.03 | 40.47 |

For all liquids except the nonpolar diiodomethane, there was a significant decrease of contact angle with time. These results were plotted and linear regression was applied to the line. The polar surface free energy component of vernix was calculated from the slope (which is equal to the square root of $Y_L^P$). The dispersive surface free energy component of vernix was calculated from the intercept (which is equal to the square root of $Y_L^D$).

The liquid total SFE, liquid polar SFE, and liquid dispersive SFE are known and are as follows:

| | Surface Tension Components (dyne/cm) | | |
|---|---|---|---|
| Liquid | Total | Dispersive | Polar |
| Benzyl Alcohol | 39 | 30.3 | 8.7 |
| Diiodomethane | 50.8 | 50.8 | 0 |
| Glycerol | 64 | 34 | 30 |
| Water | 72.8 | 21.8 | 51 |

Figure 4:
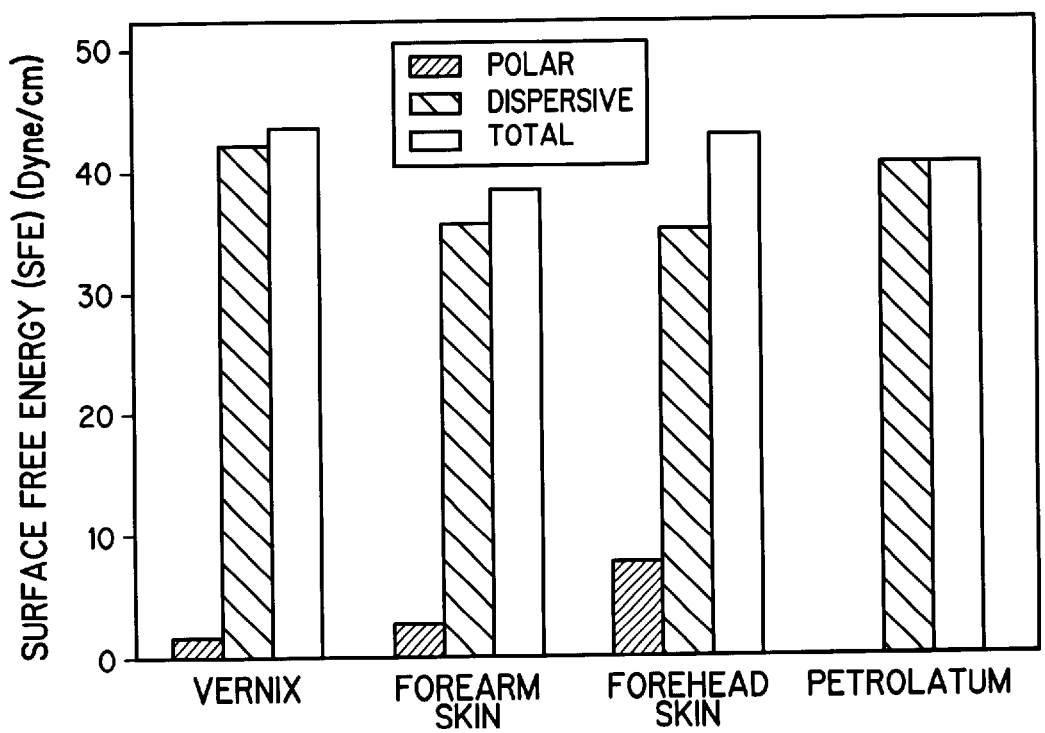
FIG. 4 is a histogram comparing the surface free energy of vernix, skin, and petrolatum.

FIG. 4 is a histogram showing the surface free energy (SFE) in dyne/cm of vernix, skin from the forearm, skin from the forehead, and petrolatum. As shown in FIG. 4, vernix, skin and petrolatum share a similar total surface free energy value. Vernix, skin and petrolatum also share a major dispersive component.

Skin is known for its superior water barrier properties. The CST of vernix was higher than the CST of skin on both the forearm (27 dyne/cm) and the finger (27 dyne/cm), but was lower than the CST of skin on the forehead (50.7 dyne/cm). The forearm, finger, and forehead vary in part due to differences in sebum level, with the forehead possessing the highest density of sebaceous glands and the highest level of sebum secretion. The high CST in forehead skin is due to the presence of sebum. In comparing the CST of forehead skin before and after extraction of sebum, sebum extraction decreased skin wettability and CST values from 50.7 dyne/cm to 29.3 dyne/cm. Degreasing and cleaning of the skin surface reduces the skin wettability and CST. The obtained CST for vernix (about 39 dyne/cm) is the approximate average of the CST for the sebum-poor forearm skin (about 27 dyne/cm) and the sebum-rich forehead skin (about 51 dyne/cm), supporting the lipid composition of vernix as a mixture of stratum corneum lipids and sebaceous lipids.

The CST of vernix is also similar to the CST of several polymers, e.g., vinyl polymers such as polyvinyl chloride (PVC, CST 39 dyne/cm), polyvinyl alcohol (37 dyne/cm), and polyvinylidene chloride (40 dyne/cm). A common use for PVC is for waterproofing in raincoats and shower curtains.

These results indicate that the main component of the vernix surface free energy was dispersive, that is, nonpolar. Fresh vernix polar SFE was 1.48 dynes/cm, while petrolatum had almost no polar SPE (0.03 dynes/cm). The polar component of vernix SFE was minimal, and the nonpolar component was substantially higher. The nonpolar component in vernix was slightly lower than that of petrolatum, which has an extremely low polar component. There was agreement between the results for fresh vernix from both static and dynamic contact angle data. The older vernix sample had comparable results but had a lower polar component, which may represent drying of the sample over seven weeks.

The CST of fresh vernix, 40.47 dyne/cm, was comparable to the CST of petrolatum, 35.79 dyne/cm, and did not differ between the two methods (dynamic contact angle and static contact angle). The CST for fresh and older vernix samples was also comparable. Given the CST, vernix is a low energy surface. The low CST of vernix is in contrast to the CST of water which was 72 dyne/cm. Vernix contains about 80% by weight of water. These results indicate that vernix has low surface energy and is highly unwettable. Although vernix is about 80% water, which is highly energetic, the major part of the vernix SFE was hydrophobic (dispersive). The limited contribution of the polar component, limiting the interaction between vernix and hydrophilic liquids, was unexpected but supportive of vernix as a natural protect which waterproofs a fetus that is continuously exposed to amniotic fluid. Because of the high water content in vernix, the high hydrophobic component of its surface free energy is due to the continuous phase of the lipids around the cellular elements.

EXAMPLE 2

Barrier repair was evaluated by determining the effect of various films on the rate of barrier repair and the quality of the barrier that was formed. The semi-permeable films are used in the health care industry and include Vigilon® (a high water content hydrogel, 96% water, covered with impermeable plastic), Silon®, Flexzan®, and Exxaire® for the treatment of compromised skin. The occlusive (control) films were Saran Wrap® and Teflon® (polyethylene terphthalate). No occlusion controls contained no film.

The Vigilon® film provided a wet, occlusive environment for compromised skin because the water-rich hydrogel was positioned against the compromised skin surface and the plastic backing provided occlusion to water loss, and was damaging to skin due to the high water exposure and complete occlusion.

The semipermeable films facilitated quantitatively better barrier recovery of the compromised skin, compared to films that resulted in either complete occlusion, no occlusion, or a high water environment plus occlusion. The skin sites that recovered under this semipermeable film developed better skin condition relative to the fully occlusive film and the no occlusion control film, and provided more favorable environment for skin during barrier recovery that the no occlusion film and the complete occlusion control film. The films that produced intermediate levels of recovered skin hydration had the highest barrier recovery values. The film created a skin hydration environment that results in different rates of barrier repair. The semipermeable film enhanced the rate of barrier repair. The semipermeable film also enhanced the quality of the recovered skin. These enhancements were due to the semipermeable film facilitating the optimum water vapor gradient during the recovery process of the compromised skin.

Figure 5:
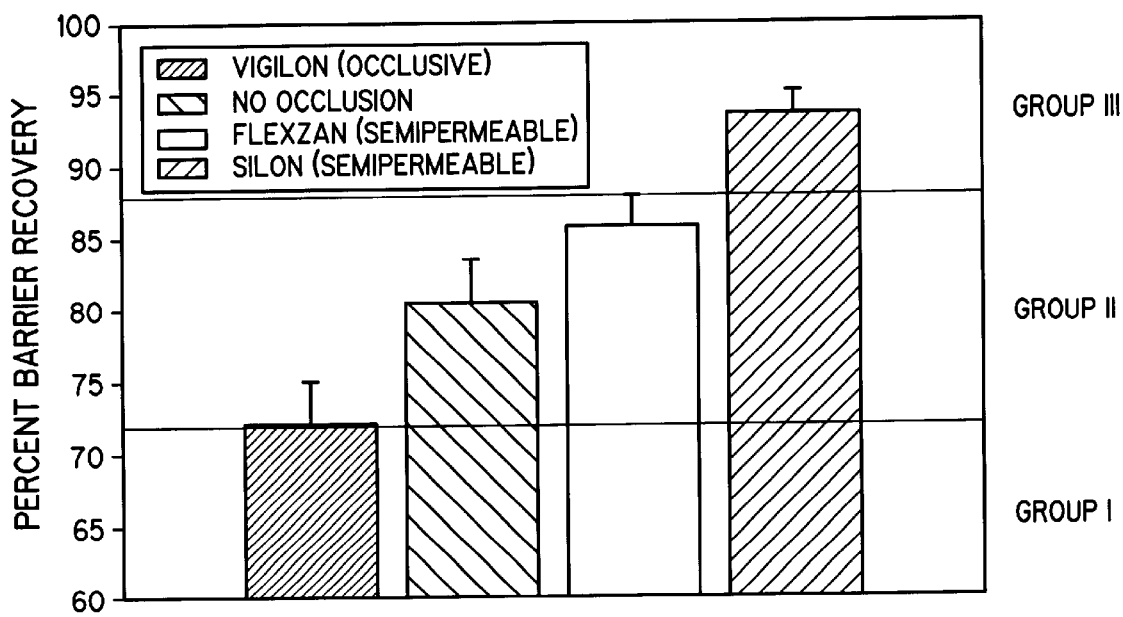
FIG. 5 is a graph showing percent barrier recovery using various films.
Figure 6:
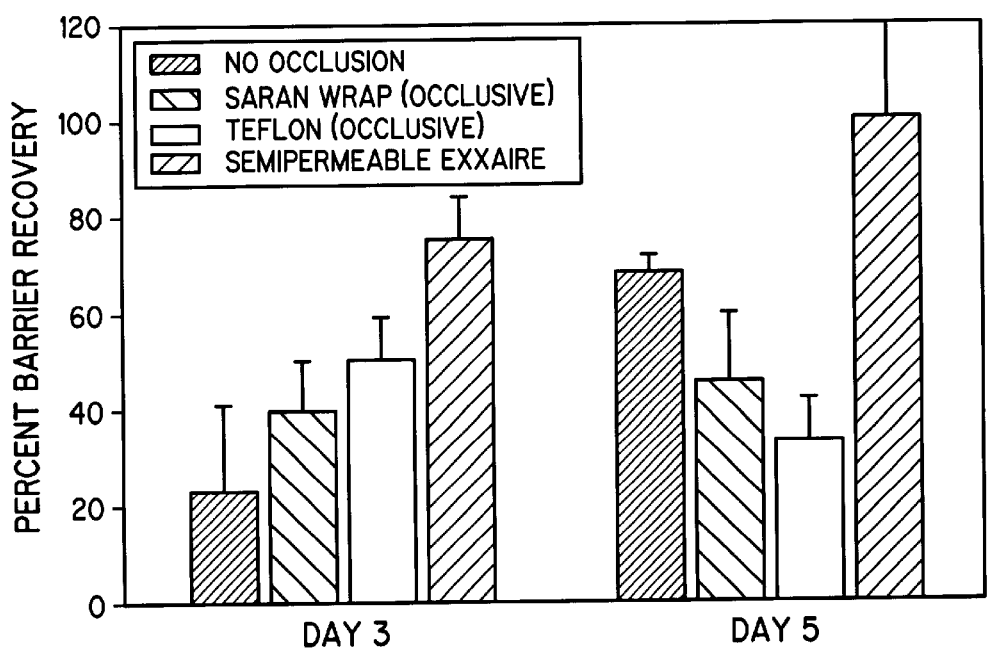
FIG. 6 is a histogram of the effect of various films on percent barrier recovery.
Figure 7:
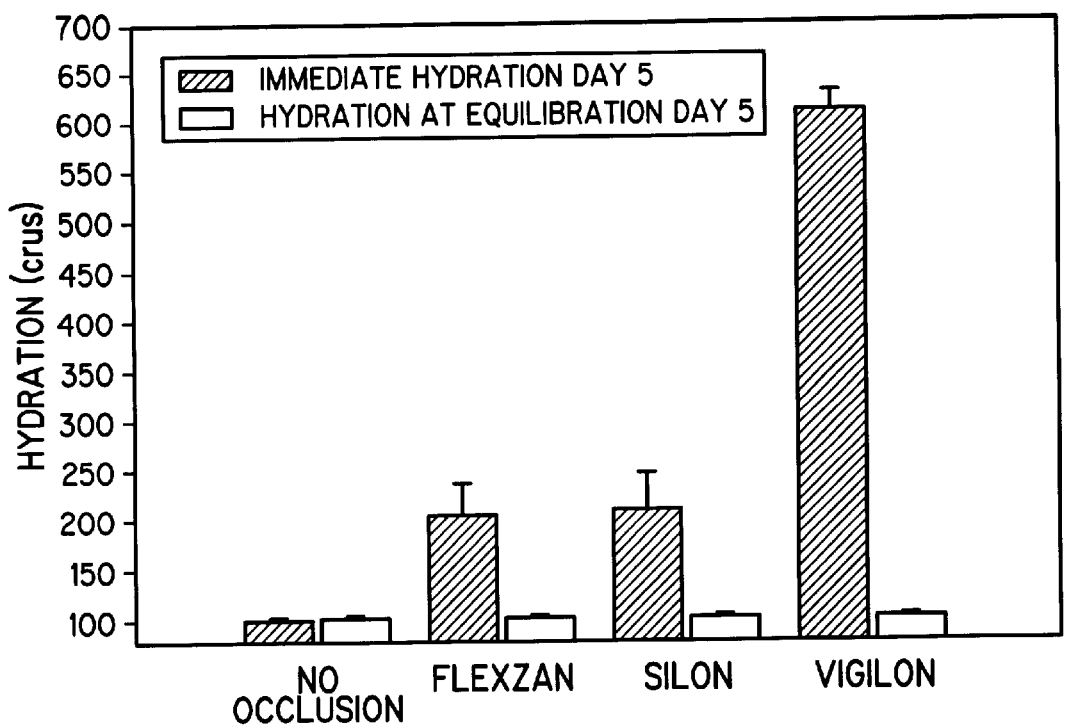
FIG. 7 is a histogram showing various films and the hydration of skin in contact with those films.
Figure 8:
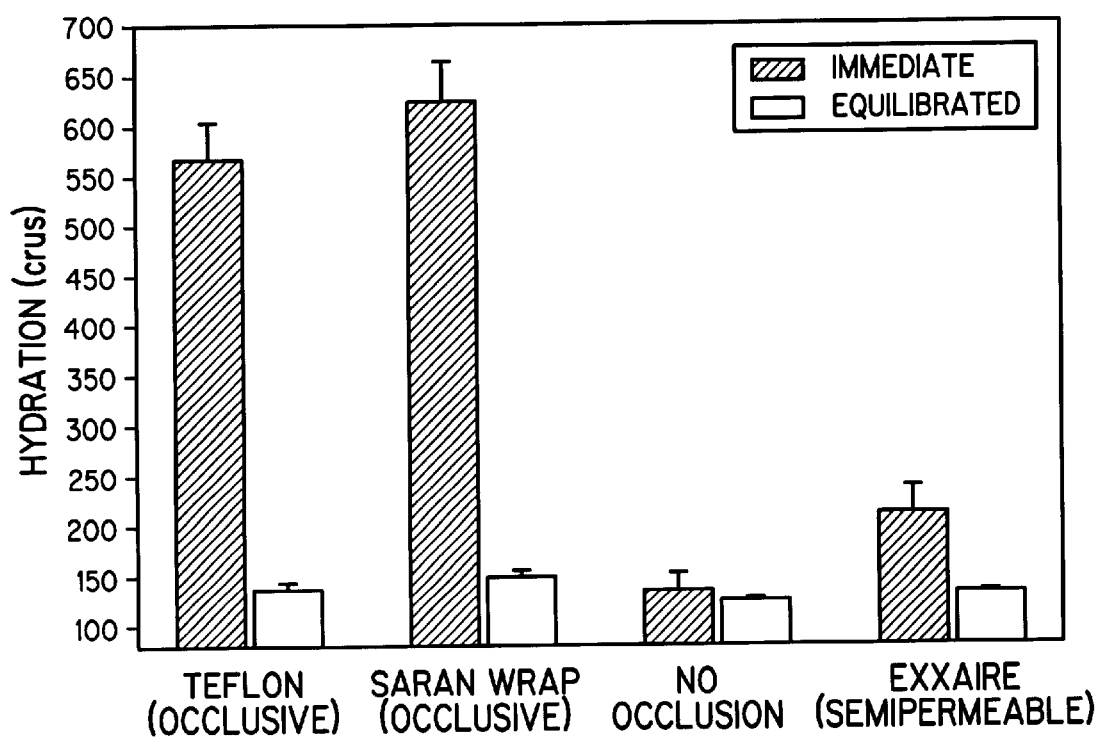
FIG. 8 is a histogram showing various films and the hydration of skin in contact with those films.
Figure 9:
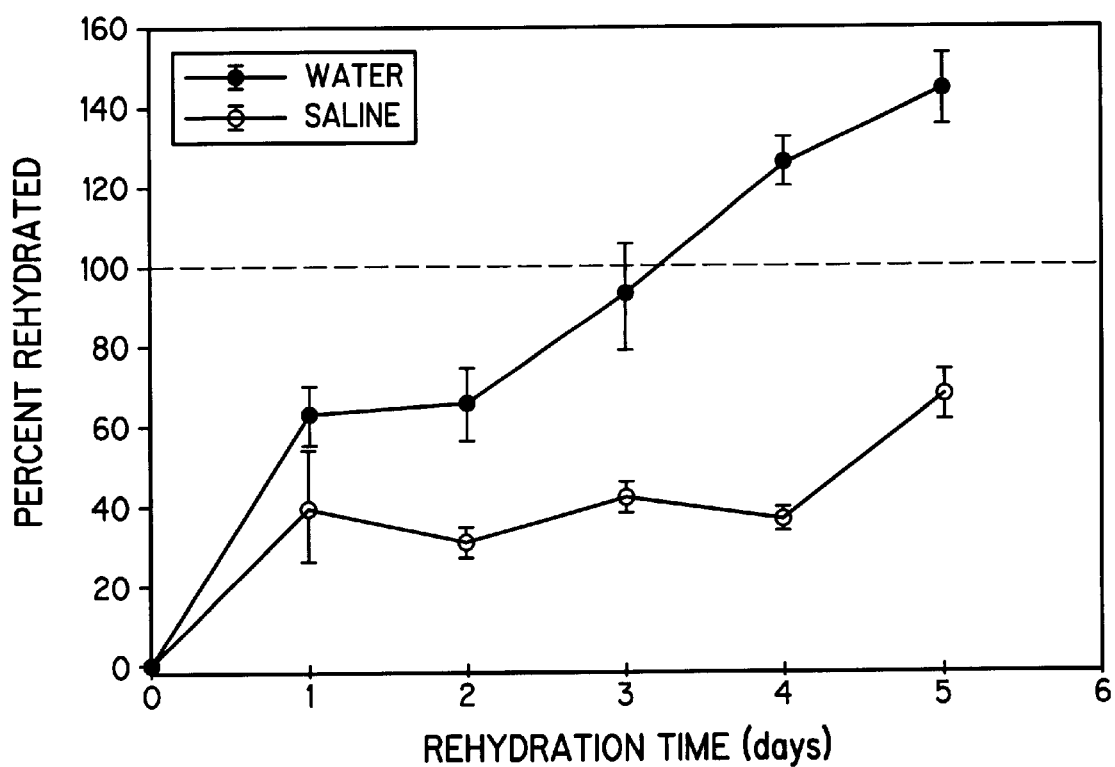
FIG. 9 is a graph showing rehydration of vernix.
Figure 10:
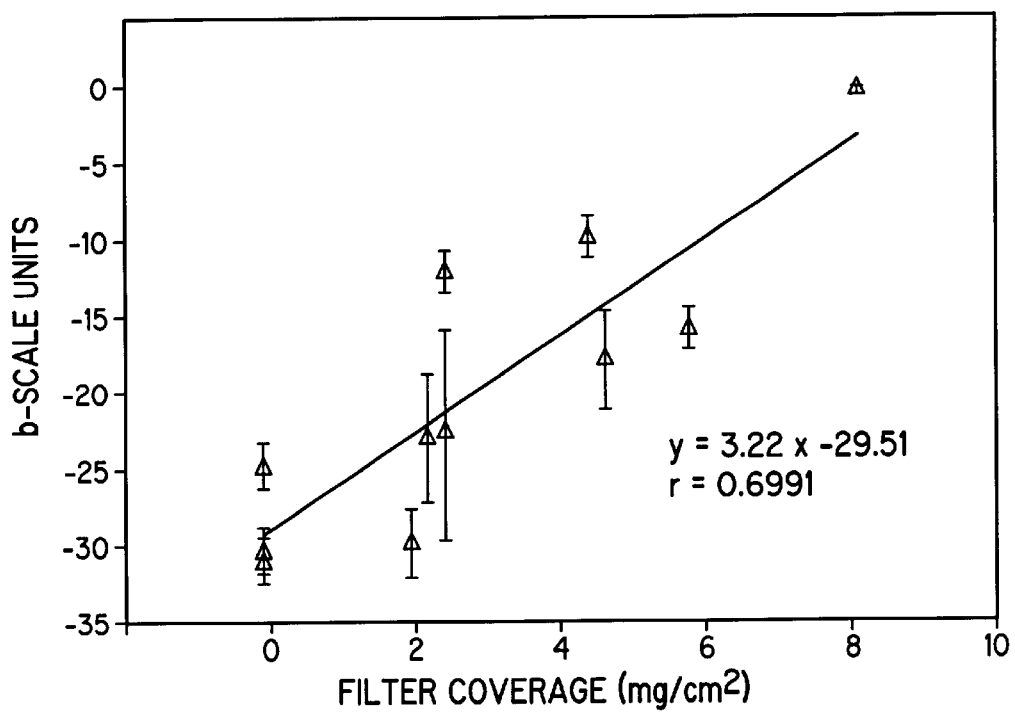
FIG. 10 is a graph of Hunter b-scale measurements by Minolta chromameter of methylene blue dye on collagen film protected by DMSO-treated vernix covered nylon filters.
Figure 11:
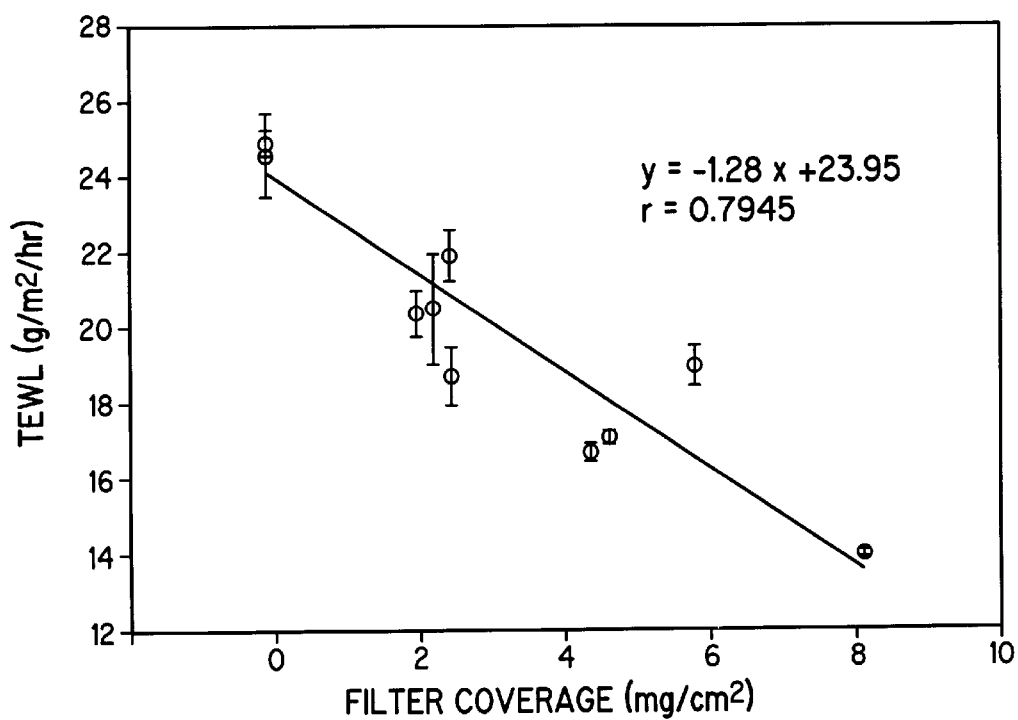
FIG. 11 is a graph of water vapor permeation rate (transepidermal water loss) measurements of nylon filters coated with DMSO-treated vernix.

FIG. 5 shows that the semipermeable films result in a higher percent barrier than no occlusion and Vigilon®. FIG. 6 shows that the semipermeable Exxaire® has a significantly higher percent barrier recovery than no occlusion and the occlusive films. FIG. 7 shows that Vigilon® provided a very high level of water when in contact with the skin. In contrast, the semipermeable films provided an intermediate level of hydration. In further contrast, the semipermeable films produced higher hydration than no occlusion. As a result, an intermediate level of hydration provides the optimum environment for barrier repair to occur, compared to either a high or low level of hydration. FIG. 8 shows, again, that the semipermeable film Exxaire® provided an intermediate level of hydration, in comparison to no occlusion and to the high hydration produced by the occlusive films. FIG. 9 demonstrates that vernix can be effectively rehydrated when exposed to water or saline.

The action of vernix is similar to that of the semipermeable film. A vernix film is not fully occlusive. Vernix contains about 80% water and, unlike stratum corneum, it does not have desmosomal attachments between cells and its lipid phase is not as structured as in stratum corneum. Therefore, water is transported through vernix in much the same way as water vapor is transported through a semipermeable film. Vernix regulates the water or hydration environment of the skin during repair, controlling the water environment to which the skin is exposed. Thus, application of vernix to compromised skin provides an optimum water gradient to the skin surface. The high water content of vernix, associated with the cellular components, provides a supply of water to tissues during barrier repair, barrier formation, and compromised skin healing or repair processes. Vernix also retains its water, and loses water to the environment only very slowly, as shown in measurements of weight changes in vernix over time. Thus, vernix provides a source of water but also releases some water to the environment.

Vernix also rehydrates by uptake of water during water exposure. Normal adult skin with vernix applied to the skin surface (treated) had a higher rate of water loss than skin to which no vernix was applied (control), demonstrating that vernix released water from the skin surface. Measurements of peak sorption indicated that the vernix treated skin binds water to a significantly greater extent than that of untreated skin, and had a significantly higher water binding capacity than untreated skin. Vernix takes up water from a wet epidermal surface, for example, a skin wound, and moves it away from the surface or wound, for example, into cells. These hydration properties of vernix, both dehydration and rehydration, allow vernix to function in both wet and dry environments. Vernix accordingly can either give up water, or take up water, using physiological control mechanisms such as water binding of proteins and soluble materials in the cells.

EXAMPLE 3

A dispersion of 20%$^{w/v}$ vernix in 100% DMSO was prepared with sonication and agitation to form a homogenous mixture. Nine 2-mm holes were drilled into the bottom of each well of a standard six-well polystyrene tissue culture plate (Becton Dickinson Labware, Bedford, Mass.). A singular circular sterile nylon filter, 20 micron porosity, 25-mm diameter (Micron Separations Inc., Westboro, Mass.) was placed into each well. The nylon filters were coated with vernix by first pipetting one ml of the 20%$^{w/v}$ vernix solution onto the top of each filter. Excess liquid was then wicked out of the wells through the filters on the bottom of the plate using paper towels. Finally the remainder of the liquid was evaporated by placing the culture plate in a vacuum chamber for a period of between 72 and 168 hours. The vernix-coated filters were then sterilized by gamma-irradiation at 17 kGy for use in skin culture.

Cultures of human skin were prepared by a standard technique inoculating human keratinocytes onto a fibroblast-impregnated collagen-glycosaminoglycan support. Cultures were assessed weekly for epidermal barrier formation by surface electrical capacitance using a dermal phase meter (Nova Technology Corporation, Gloucester, Mass.) and were sampled weekly for histology and mitochondrial enzyme activity. In addition, the conditioned culture medium was sampled daily for glucose and lactate levels. In one embodiment, three-day old cultured human skin substitutes were overlaid with the vernix coated nylon filter.

The following data were obtained following Example 3.
Methylene blue dye exclusion
  I. Support materials
    The coated support materials were Magna nylon filters, pore size 20 microns, manufacured by Micron Separations Inc. (see Fisher Scientific)
    Circular discs were punched out of the nylon filters (surface area 2.84-cm 2; r=0.95 cm) and coated with DMSO-dispensed vernix as described below.
    Each coated nylon discs was place over a piece of collagen film (49-cm 2; 7 cm×7 cm) that had been obtained from Viscofan, USA, Inc.
    The collagen film had been pre-equilbrated at 41% RH at 24 oC overnight.
  II. Test film coverage
    Vernix was dispersed in 10 volumes of dimethyl sulfoxide (DMSO) and pipelled onto circular nylon fiber discs.
    The DMSO solvent was evaporated under room temperature vacuum.
    The coating of vernix on the nylon filters ranged between 0.04 DMSO-coated blank) and 6.17 mg/cm 2.
  III. Methylene blue dye
    Methylene blue dye was made up tp 0.5% (w/v) in ddH2O.
    The coated nylon disc was placed on a square of pre-eqilgrated collagen film (see above).
    A single circle of methylene blue dye was pipelled onto the coated nylon support surface.
    After 30 minutes, the methylene blue dye was carefully blotted off of the nylon disc with absorbent tissue.
  IV. Measurement
    Measurement 1: The (coated) blotted nylon disc was removed and a mask was placed over the underlying collagen film that covered all of the collagen surface except for the area that had been in contact with the nylon filter. A Minolta chromameter was than used to record Hunter L-, a-, b-scale measurements from the surface of the exposed collagen film at three unique sites.

Measurement #2: A new piece of the collagen film was placed over a reservoir of dd H2O at room temperature (23oC) and 41% RH.

One of the previously (coated) blotted nylon discs was place on the new collagen film support and transepidermal water loss (TEWL) date were collected over a 60 second Interval using a Dermal Lab evaporimeier (Cortex Technology).

The evaporimeter was connected to a Compaq Armada 4120 laptop computer and controlled by cyberDERM software (CyberDerm, Inc.).

RAW DATA-UNSORTED

| filter # (-) | | pre-coated wgt (mg) | post-coated wgt (mg) | surface area (mg) | Hunter b-scale read #1 (-) | read #2 (-) | read #3 (-) | TEWL read #1 (g/m2/h) | read #2 (g/m2/h) | read #3 (g/m2/h) |
|---|---|---|---|---|---|---|---|---|---|---|
| 1 | (blank) | 10.2 | 10.3 | 2.64 | −25.47 | −25.98 | −23.19 | 24.5 | 25.0 | 24.5 |
| 2 | (blank) | 10.4 | 10.5 | 2.64 | −29.07 | −32.60 | −30.45 | 24.4 | 25.5 | 24.4 |
| 3 | (blank) | 10.6 | 10.7 | 2.64 | −32.79 | −29.70 | −30.69 | 22.3 | 25.3 | 25.8 |
| 4 | | 10.5 | 17.8 | 2.84 | −16.35 | −22.32 | −29.88 | 17.2 | 18.6 | 20.0 |
| 5 | | 10.7 | 16.7 | 2.84 | −29.71 | −32.31 | −27.79 | 20.8 | 21.2 | 19.1 |
| 6 | | 10.7 | 17.3 | 2.84 | −20.11 | −21.19 | −27.94 | 17.5 | 21.7 | 22.0 |
| 7 | | 10.7 | 24.1 | 2.84 | −20.69 | −18.77 | −14.35 | 16.7 | 17.1 | 17.0 |
| 8 | | 10.9 | 23.6 | 2.84 | −8.74 | −11.42 | −9.50 | 18.2 | 16.4 | 17.0 |
| 9 | | 10.4 | 17.6 | 2.84 | −10.74 | −12.11 | −13.48 | 20.4 | 22.5 | 22.5 |
| 10 | | 10.7 | 33.0 | 2.84 | −0.44 | 0.00 | −0.51 | 13.7 | 13.8 | 14.0 |
| 11 | | 10.5 | 27.2 | 2.84 | −16.44 | −16.60 | −14.59 | 17.9 | 19.8 | 18.9 |
| no filter | | na | na | na | na | na | na | 26.4 | 26.3 | 26.7 |

HUNTER b-SCALE DATA SORTED BY FILTER COVERAGE

| filter # (-) | | pre-coated wgt (mg) | post-coated wgt (mg) | coating wgt (mg) | coverage (mg/cm2) | read #1 (-) | read #2 (-) | read #3 (-) | mean (-) | sem (-) |
|---|---|---|---|---|---|---|---|---|---|---|
| 1 | (blank) | 10.2 | 10.3 | 0.1 | 0.04 | −25.47 | −25.98 | −23.19 | −24.88 | 0.86 |
| 2 | (blank) | 10.4 | 10.5 | 0.1 | 0.04 | −29.07 | −32.50 | −30.45 | −30.71 | 1.03 |
| 3 | (blank) | 10.8 | 10.7 | 0.1 | 0.04 | −32.79 | −29.70 | −30.59 | −31.03 | 0.92 |
| 5 | | 10.7 | 18.7 | 5.0 | 2.11 | −29.71 | −32.31 | −27.79 | −29.94 | 1.31 |
| 6 | | 10.7 | 17.3 | 6.6 | 2.32 | −20.11 | −21.19 | −27.94 | −23.08 | 2.45 |
| 9 | | 10.4 | 17.6 | 7.2 | 2.54 | −10.74 | −12.11 | −13.46 | −12.10 | 0.79 |
| 4 | | 10.5 | 17.6 | 7.3 | 2.57 | −16.35 | −22.32 | −29.86 | −22.84 | 3.91 |
| 8 | | 10.9 | 23.6 | 12.7 | 4.47 | −8.74 | −11.42 | −9.50 | −9.89 | 0.80 |
| 7 | | 10.7 | 24.1 | 13.4 | 4.72 | −20.69 | −18.77 | −14.35 | −17.94 | 1.88 |
| 11 | | 10.5 | 27.2 | 16.7 | 5.88 | −18.44 | −16.50 | −14.59 | −15.88 | 0.54 |
| 10 | | 10.7 | 33.9 | 23.2 | 8.17 | −0.44 | 0.00 | −0.51 | −0.32 | 0.18 |

WATER/VAPOR PERMEATION RATE (TEWL) DATA SORTED BY FILTER COVERAGE

| filter # (-) | | pre-coated wgt (mg) | post-coated wgt (mg) | coating wgt (mg) | coverage (mg/cm2) | read #1 (g/m2/h) | read #2 (g/m2/h) | read #3 (g/m2/h) | mean (g/m2/h) | sem (g/m2/h) |
|---|---|---|---|---|---|---|---|---|---|---|
| 1 | (blank) | 10.2 | 10.3 | 0.1 | 0.04 | 24.5 | 25.0 | 24.5 | 24.67 | 0.17 |
| 2 | (blank) | 10.4 | 10.5 | 0.1 | 0.04 | 24.4 | 25.5 | 24.4 | 24.77 | 0.37 |
| 3 | (blank) | 10.6 | 10.7 | 0.1 | 0.04 | 22.3 | 25.3 | 25.8 | 24.47 | 1.09 |
| 5 | | 10.7 | 16.7 | 8.0 | 2.11 | 20.6 | 21.2 | 19.1 | 20.30 | 0.62 |
| 6 | | 10.7 | 17.3 | 8.6 | 2.32 | 17.6 | 21.7 | 22.0 | 20.40 | 1.45 |
| 9 | | 10.4 | 17.6 | 7.2 | 2.54 | 20.4 | 22.5 | 22.5 | 21.80 | 0.70 |
| 4 | | 10.5 | 17.8 | 7.3 | 2.57 | 17.2 | 18.6 | 20.0 | 18.60 | 0.81 |
| 8 | | 10.9 | 23.6 | 12.7 | 4.47 | 18.2 | 16.4 | 17.0 | 16.53 | 0.24 |
| 7 | | 10.7 | 24.1 | 13.4 | 4.72 | 16.7 | 17.1 | 17.0 | 18.93 | 0.12 |
| 11 | | 10.5 | 21.7 | 16.7 | 5.88 | 17.9 | 19.8 | 18.9 | 18.87 | 0.55 |
| 10 | | 10.7 | 33.9 | 23.2 | 8.17 | 13.7 | 13.8 | 14.0 | 13.83 | 0.09 |
| no filter | | na | na | | | 26.4 | 26.3 | 26.7 | 26.47 | 0.12 |

A nontoxic vernix film and methods of producing and using the film are thus disclosed. The compositions and methods of the invention may be used for providing a biological waterproofing surface. Other variations or embodiments of the invention will also be apparent to one of ordinary skill in the art from the above description and example. For example, vernix may be formulated into a cream, such as a first aid cream, a cream for treating poison ivy or other forms of contact dermatitis, or a diaper rash cream, or other formulations such as a paste, lotion, gel, ointment, cream, etc. Thus, the forgoing embodiments are not to be construed as limiting the scope of this invention.

What is claimed is:

1. A method to regulate skin hydration comprising applying a composition consisting essentially of vernix and a dispersing agent to skin in an amount effective to regulate hydration.
2. The method of claim 1 wherein said skin is developing skin.
3. The method of claim 2 wherein said developing skin is an epidermal surface.
4. The method of claim 3 wherein said epidermal surface is undergoing terminal differentiation to produce a cornified layer.
5. The method of claim 2 wherein said developing skin is a wound.
6. The method of claim 5 wherein said regulation comprises wound healing.
7. The method of claim 2 wherein said developing skin is on a newborn.
8. The method of claim 1 wherein said composition regulates hydration by giving up water.
9. The method of claim 1 wherein said composition regulates hydration by taking up water.
10. The method of claim 1 wherein said composition is regulated to contain an increased polar component.
11. The method of claim 1 wherein said composition is regulated by removing a lipid fraction from vernix.
12. A method to regulate skin hydration comprising regulating a water gradient of skin by applying a composition consisting essentially of vernix to skin in an amount to control said water gradient.
13. The method of claim 12 wherein said water gradient regulation is for skin moisture retention.
14. The method of claim 12 wherein said water gradient is for skin barrier function.
15. The method of claim 12 wherein said amount of vernix is a film having a thickness from about 10 $\mu$m to about 500 $\mu$m.
16. The method of claim 15 wherein said film thickness increases water retention in said skin.
17. A method of lowering the rate of water vapor transmission of a surface comprising applying a composition consisting essentially of vernix to said surface.
18. The method of claim 17 wherein vernix is applied as a film.
19. The method of claim 17 wherein vernix is applied to a surface selected from the group consisting of skin, cornea, vagina, gastrointestinal tract, buccal cavity, mucous membranes, and combinations thereof.
20. The method of claim 17 wherein said surface is cells growing in vivo.
21. The method of claim 17 wherein said surface is cells growing in vitro.
22. The method of claim 19 wherein vernix is applied as a film having a thickness from about 10 $\mu$m to about 500 $\mu$m.
23. The method of claim 22 wherein increasing said film thickness decreases water vapor transmission in said surface.
24. The method of claim 17 wherein said vernix is selected from the group consisting of a natural vernix and a synthetic vernix.
25. The method of claim 19 wherein said surface is a support.

* * * * *

UNITED STATES PATENT AND TRADEMARK OFFICE
CERTIFICATE OF CORRECTION

PATENT NO.   : 6,562,358 B2
DATED        : May 13, 2003
INVENTOR(S)  : Hoath et al.

It is certified that error appears in the above-identified patent and that said Letters Patent is hereby corrected as shown below:

Column 1,
Lines 7-8, change "...filed May 10, 2000, which is a Continuation-In-Part..." to
-- ...filed May 10, 2000, and is a Continuation-In-Part... --

Signed and Sealed this

Fourth Day of January, 2005

JON W. DUDAS
*Director of the United States Patent and Trademark Office*